(12) United States Patent
Hara et al.

(10) Patent No.: US 9,570,879 B2
(45) Date of Patent: Feb. 14, 2017

(54) OPTICAL PULSE-GENERATOR AND OPTICAL PULSE-GENERATING METHOD

(71) Applicant: Sumitomo Osaka Cement Co., Ltd., Tokyo (JP)

(72) Inventors: Tokutaka Hara, Tokyo (JP); Youichi Hosokawa, Tokyo (JP)

(73) Assignee: Sumitomo Osaka Cement Co., Ltd., Tokyo (JP)

( * ) Notice: Subject to any disclaimer, the term of this patent is extended or adjusted under 35 U.S.C. 154(b) by 205 days.

(21) Appl. No.: 14/384,550

(22) PCT Filed: Mar. 14, 2013

(86) PCT No.: PCT/JP2013/057172
§ 371 (c)(1),
(2) Date: Sep. 11, 2014

(87) PCT Pub. No.: WO2013/137384
PCT Pub. Date: Sep. 19, 2013

(65) Prior Publication Data
US 2015/0029575 A1    Jan. 29, 2015

(30) Foreign Application Priority Data

Mar. 14, 2012  (JP) .................................. 2012-057723
Sep. 24, 2012  (JP) .................................. 2012-209614

(51) Int. Cl.
*H01S 3/10*   (2006.01)
*H01S 3/13*   (2006.01)
(Continued)

(52) U.S. Cl.
CPC .. *H01S 3/11* (2013.01); *G01J 3/10* (2013.01); *G01N 21/3581* (2013.01);
(Continued)

(58) Field of Classification Search
CPC ................. G01J 3/45; G01J 3/26; G01J 3/10; G01J 3/453; G01J 3/0205; G01J 9/02; G01J 3/0291; G01J 11/00; G01J 3/2823; G01J 2009/0288; G02F 2203/50; G02F 1/01
(Continued)

(56) References Cited

U.S. PATENT DOCUMENTS 6,809,849 B2 * 10/2004 Akiyama .............. G02F 1/0121
359/237

FOREIGN PATENT DOCUMENTS

JP    2001512861 A    8/2001
JP    2004064097 A    2/2004
(Continued)

OTHER PUBLICATIONS

Japanese Patent Office, International Search Report issued in corresponding International Patent Application No. PCT/JP2013/057172 and English-language translation, mailed Apr. 16, 2013 (4 pages).
(Continued)

*Primary Examiner* — Evelyn A Lester
(74) *Attorney, Agent, or Firm* — Wood Herron & Evans LLP

(57) ABSTRACT

Provided is an optical pulse-generator and an optical pulse-generating method which are capable of generating an optical pulse train with an arbitrary pattern. An optical pulse-generator 1 includes a first optical modulator 21 configured to modulate input light using a first modulation signal SIG1 to generate optical pulses, a second optical modulator 41 configured to perform a modulation operation using a second modulation signal SIG2 synchronizing with the first modulation signal SIG1 and having a signal pattern that is set to output only specific part of the optical pulses,
(Continued)

and a dispersion compensator 30 configured to compensate a chirp of the optical pulse output from the first optical modulator 21.

14 Claims, 10 Drawing Sheets

(51) Int. Cl.
*G01B 9/02* (2006.01)
*G02F 1/01* (2006.01)
*H01S 3/11* (2006.01)
*G01J 3/10* (2006.01)
*G01N 21/3581* (2014.01)
*H01S 3/00* (2006.01)
*G01J 3/26* (2006.01)
*G01J 3/02* (2006.01)
*G01J 9/02* (2006.01)
*G01J 3/45* (2006.01)
*G01J 11/00* (2006.01)
*G01J 3/28* (2006.01)
*G01J 3/453* (2006.01)
*G02F 1/21* (2006.01)
*G02F 1/225* (2006.01)
*H01S 3/067* (2006.01)
*H01S 5/12* (2006.01)

(52) U.S. Cl.
CPC .......... *G02F 1/2252* (2013.01); *H01S 3/0057* (2013.01); *H01S 3/0085* (2013.01); *H01S 3/1301* (2013.01); *G01J 3/0205* (2013.01); *G01J 3/0291* (2013.01); *G01J 3/26* (2013.01); *G01J 3/2823* (2013.01); *G01J 3/45* (2013.01); *G01J 3/453* (2013.01); *G01J 9/02* (2013.01); *G01J 11/00* (2013.01); *G01J 2009/0288* (2013.01); *G02F 1/01* (2013.01); *G02F 1/21* (2013.01); *G02F 1/2255* (2013.01); *G02F 1/2257* (2013.01); *G02F 2001/212* (2013.01); *G02F 2201/16* (2013.01); *G02F 2203/13* (2013.01); *G02F 2203/50* (2013.01); *G02F 2203/56* (2013.01); *H01S 3/06754* (2013.01); *H01S 5/12* (2013.01); *H01S 2301/08* (2013.01)

(58) Field of Classification Search
USPC . 372/25, 29.02; 356/450, 451, 477; 359/279
See application file for complete search history.

(56) References Cited

FOREIGN PATENT DOCUMENTS

| | | |
|---|---|---|
| JP | 2006184851 A | 7/2006 |
| JP | 2007516600 A | 6/2007 |
| JP | 2007248660 A | 9/2007 |
| JP | 2009175576 A | 8/2009 |
| JP | 2011180192 A | 9/2011 |
| JP | 2012032438 A | 2/2012 |

OTHER PUBLICATIONS

Japanese Patent Office, Notice of Reasons for Rejection issued in corresponding Japanese Patent Application No. 2012-209614 and English-language translation mailed Apr. 16, 2013 (6 pages).
Japanese Patent Office, Notice of Allowance issued in corresponding Japanese Patent Application No. 2012-209614 and English-language translation mailed Aug. 20, 2013 (6 pages).

* cited by examiner

OPTICAL PULSE-GENERATOR AND OPTICAL PULSE-GENERATING METHOD

TECHNICAL FIELD

The present invention relates to an optical pulse-generator and an optical pulse-generating method.

Priority is claimed on Japanese Patent Application No. 2012-057723, filed on Mar. 14, 2012, and Japanese Patent Application No. 2012-209614, filed on Sep. 24, 2012, the contents of which are incorporated herein by reference.

BACKGROUND ART

In the past, as a technique that generates an optical pulse, a method is known in which a light is modulated to produce an optical frequency comb made up of a number of high-order frequency components, thereby turns the light into pulses, and furthermore, the optical pulse is compressed by using a dispersion compensator (for example, refer to PTL 1).

However, in the method of the related art, while it is possible to change the repetition frequency of an optical pulse, it is not possible to generate an optical pulse train with an arbitrary pattern.

CITATION LIST

Patent Literature

[PTL 1] Japanese Laid-open Patent Publication No. 2009-175576

SUMMARY OF INVENTION

Technical Problem

In an aspect of the present invention, an optical pulse-generator and an optical pulse-generating method which are capable of generating an optical pulse train with an arbitrary pattern are provided.

Solution to Problem

An optical pulse-generator of an aspect of the present invention may include a first optical modulator configured to modulate input light using a first modulation signal to generate optical pulses, a second optical modulator configured to perform a modulation operation using a second modulation signal synchronizing with the first modulation signal and having a signal pattern that is set to output only specific part of the optical pulses, and a dispersion compensator configured to compensate a chirp of the optical pulse output from the first optical modulator.

In addition, in the optical pulse-generator of the aspect of the invention, either or both of the first optical modulator and the second optical modulator may be a lithium niobate (LN) modulator.

In addition, in the optical pulse-generator of the aspect of the invention, the dispersion compensator may be disposed behind the first optical modulator and ahead of or behind the second optical modulator.

In addition, the optical pulse-generator of the aspect of the invention may include an optical pulse compressor configured to perform a soliton compression to an optical pulse from a follower one of the second optical modulator and the dispersion compensator along the optical transmission direction.

In addition, the optical pulse-generator of the aspect of the invention may include a phase adjuster configured to perform the timing synchronization between the first optical modulator and the second optical modulator.

In addition, in the optical pulse-generator of the aspect of the invention, the above-described phase adjuster may be included in a path for the first modulation signal to be applied to the first optical modulator, and the phase adjuster may not be included in a path for the second modulation signal to be applied to the second optical modulator.

In addition, an optical pulse-generating method of another aspect of the invention may include a step (optical pulse generation step) of modulating input light using a first modulation signal to generate optical pulses, a step (modulation operation step) of performing a modulation using a second modulation signal synchronizing with the first modulation signal and having a signal pattern that is set to output only specific portion of the optical pulses, and a step (chirp compensation step) of compensating a chirp of the optical pulse from the optical pulse generation step.

In addition, the above-described optical pulse-generating method of the aspect of the invention may include a step (phase adjustment step) of performing phase adjustment for performing a timing synchronization between the optical pulse generation step and the modulation operation step.

Effects of Invention

According to the invention, it is possible to generate an optical pulse train with an arbitrary pattern.

DESCRIPTION OF EMBODIMENTS

Hereinafter, embodiments of the present invention will be described in detail with reference to the accompanying drawings.

[First Embodiment]

Figure 1:
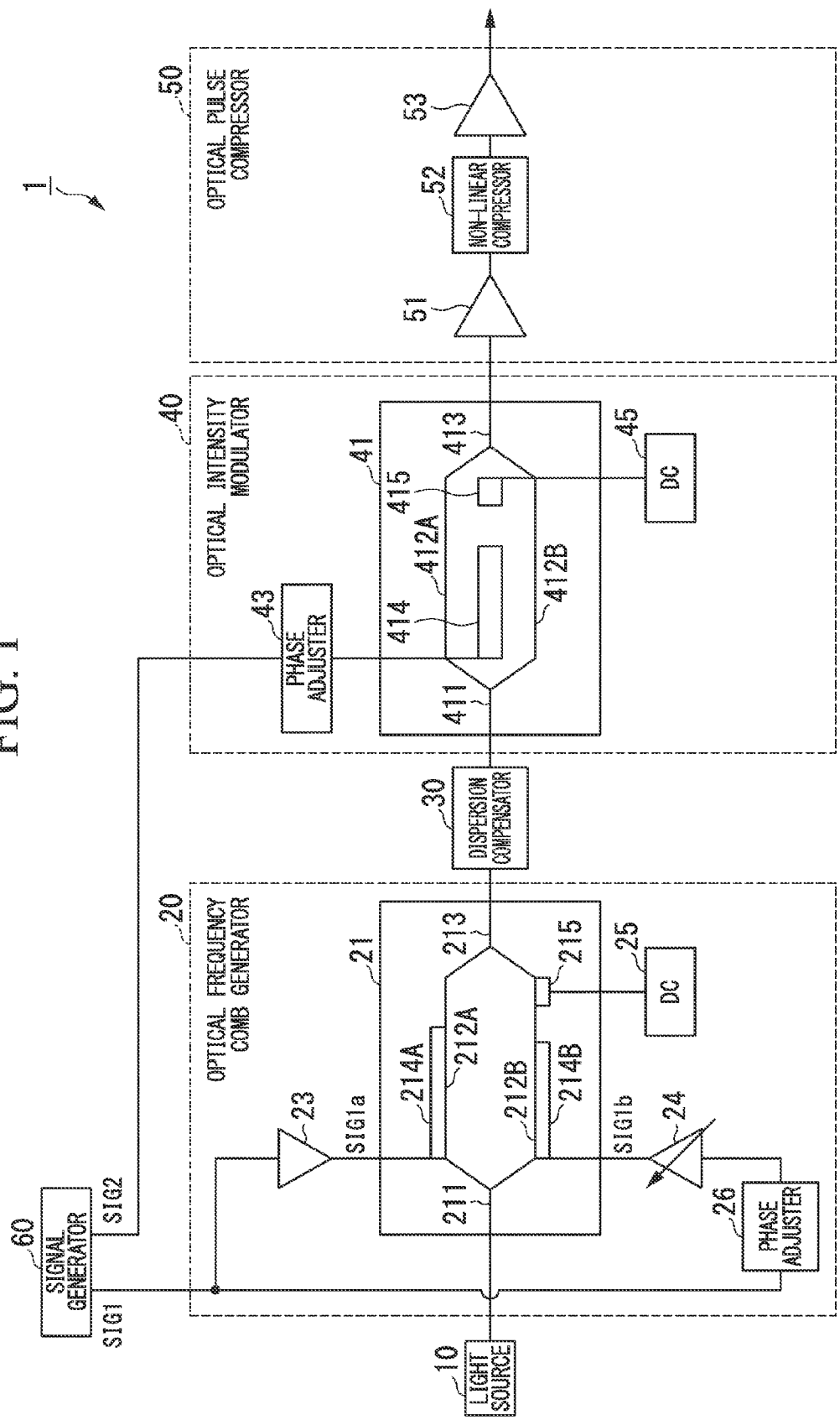
FIG. 1 is a view illustrating a configuration of an optical pulse-generator according to an embodiment (first embodiment) of the present invention.

FIG. 1 is a view illustrating the configuration of an optical pulse-generator 1 according to an embodiment (first embodiment) of the present invention.

The optical pulse-generator 1 of the first embodiment relates to terahertz time-domain spectroscopy.

The optical pulse-generator 1 includes a light source 10, an optical frequency comb generator 20, a dispersion compensator 30, an optical intensity modulator 40, an optical pulse compressor 50, and a signal generator 60.

In addition, the optical frequency comb generator 20 includes a Mach-Zehnder type optical modulator 21, an amplifier 23, a variable amplifier 24, a bias voltage supplier 25, and a phase adjuster 26. Meanwhile, the amplifier 23 and the variable amplifier 24 operate, for example, with radio frequency (RF) signals.

In addition, the optical intensity modulator 40 includes a Mach-Zehnder type optical modulator 41, a phase adjuster 43, and a bias voltage supplier 45.

In addition, the optical pulse compressor 50 includes a first optical amplifier 51, a non-linear compressor 52, and a second optical amplifier 53.

The light source 10 is, for example, a laser light source, and generates continuous light with a predetermined wavelength. As an example, distributed feedback (DFB) laser having a wavelength band of 1.55 µm can be used as the light source 10. An output end of the light source 10 is connected to an input waveguide 211 in the Mach-Zehnder type optical modulator 21 though, for example, an optical fiber.

The signal generator 60 generates a modulation signal SIG1 (for example, sinusoidal wave) having a predetermined frequency, and supplies the modulation signal to the optical frequency comb generator 20. An output which outputs the modulation signal SIG1 of the signal generator 60 is connected to the amplifier 23 and the variable amplifier 24 (through the phase adjuster 26 in the first embodiment) in the optical frequency comb generator 20. In addition, the signal generator 60 generates a modulation signal SIG2 synchronized with the modulation signal SIG1, and supplies the modulation signal to the optical intensity modulator 40. An output which outputs the modulation signal SIG2 of the signal generator 60 is connected to the phase adjuster 43 in the optical intensity modulator 40. The fact that the modulation signal SIG1 and the modulation signal SIG2 are in synchronization with each other means that the frequency of the modulation signal SIG1 and the frequency of the modulation signal SIG2 match each other, or the frequency of the modulation signal SIG2 is equal to a frequency obtained by dividing the frequency of the modulation signal SIG1 by an integer. For example, the signal generator 60 is capable of generating the modulation signals SIG1 and SIG2 like this by multiplying the frequency of a common master clock generated in its inside. The detail of the modulation signals SIG1 and SIG2 will be described later. Meanwhile, a signal generator generating the modulation signal SIG1 and a signal generator generating the modulation signal SIG2 may be separately provided. In addition, regarding to the modulation signal SIG2, it is not necessary to be constant frequency over multiple periods and may be different in each period. That is, the length of a period (the time between the adjacent peaks of the modulation signal SIG2) at a certain time and the length of the subsequent period may be different.

The Mach-Zehnder type optical modulator 21 includes the input waveguide 211, two branching waveguides 212A and 212B, an output waveguide 213, modulation electrodes 214A and 214B, and a bias electrode 215. The branching waveguides 212A and 212B are connected to the input waveguide 211 and the output waveguide 213 respectively. The output waveguide 213 is connected to an input end of the dispersion compensator 30. A Mach-Zehnder interferometer is configured by the input waveguide 211, the branching waveguides 212A and 212B, and the output waveguide 213. The modulation electrode 214A is formed on the branching waveguide 212A, and the modulation electrode 214B is formed on either or both of the branching waveguides 212A and 212B. The bias electrode 215 is formed on the branching waveguide 212B. As the Mach-Zehnder type optical modulator 21, for example, an LN modulator having the respective waveguides and the respective electrodes formed on a Z-cut LN substrate can be used. By the above-described configuration, the Mach-Zehnder type optical modulator 21 can independently control the phase of light propagating in each of two branching waveguides 212A and 212B.

Here, the LN modulator that is used as the Mach-Zehnder type optical modulator 21 is simply an example of the optical modulator, and other type of optical modulator such as a modulator in which a semiconductor such as InP is used may be used as the Mach-Zehnder type optical modulator 21.

The amplifier 23 amplifies the modulation signal SIG1 from the signal generator 60 at a predetermined amplification factor. An output of the amplifier 23 is connected to the modulation electrode 214A in the Mach-Zehnder type optical modulator 21. The variable amplifier 24 amplifies the modulation signal SIG1 from the signal generator 60 (input through the phase adjuster 26 in the first embodiment) at a predetermined amplification factor. An output of the variable amplifier 24 is connected to the modulation electrode 214B in the Mach-Zehnder type optical modulator 21. The amplification factors of the amplifier 23 and the variable amplifier 24 are set so that the amplitude of the modulation signal SIG1 applied to the modulation electrodes 214A and 214B satisfies the condition of a formula (10) described later.

The bias voltage supplier 25 supplies a bias voltage to the Mach-Zehnder type optical modulator 21. The bias voltage is set so that the condition of a formula (11) described later is satisfied. An output of the bias voltage supplier 25 is connected to the bias electrode 215 in the Mach-Zehnder type optical modulator 21.

The phase adjuster 26 matches the length of the signal path to the modulation electrode 214A and the length of the signal path to the modulation electrode 214B in order to match the phases of a modulation signal SIG1$a$ being applied to the modulation electrode 214A and a modulation signal SIG1$b$ being applied to the modulation electrode 214B.

The dispersion compensator 30 has predetermined (described later) dispersion characteristics, and compresses an optical pulse (described later) from the optical frequency comb generator 20, and outputs the compressed optical pulse. As the dispersion compensator 30, for example, an optical fiber having the above-described predetermined dispersion characteristics can be used, and an optical element other than the optical fiber may also be used.

Meanwhile, generally, the dispersion compensator 30 is disposed behind (not necessarily just behind) the optical frequency comb generator 20.

Figure 5A:
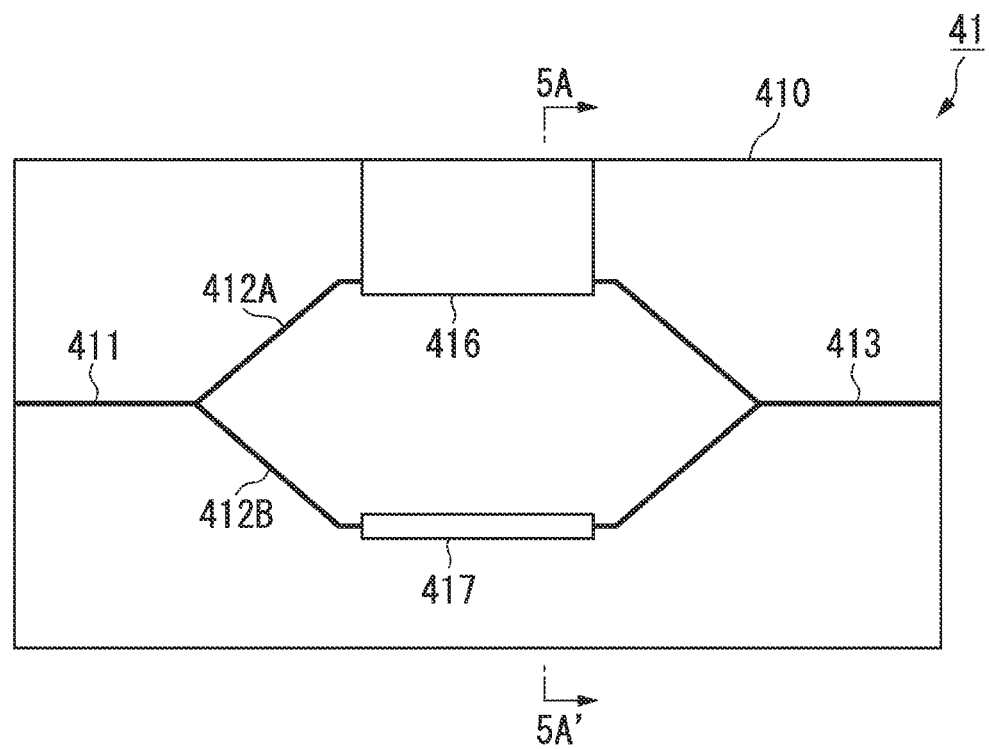
FIG. 5A is a view illustrating an electrode layout in a Mach-Zehnder type optical modulator 41 in which a Z-cut LN substrate is used.
Figure 5B:
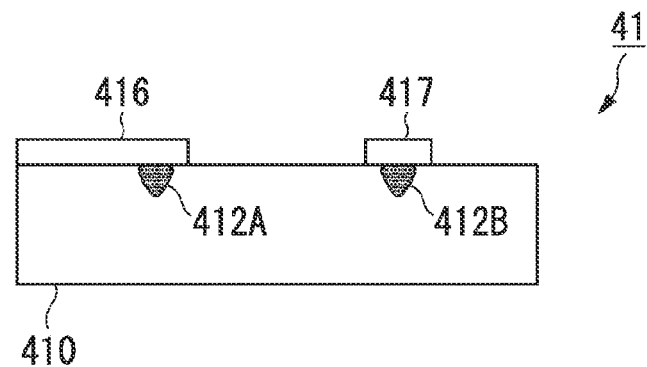
FIG. 5B is a cross-sectional view cut along the line 5A-5A' in FIG. 5A.

The Mach-Zehnder type optical modulator 41 includes an input waveguide 411, two branching waveguides 412A and 412B, an output waveguide 413, a modulation electrode 414, and a bias electrode 415. The input waveguide 411 is connected to an output end of the dispersion compensator 30. The branching waveguides 412A and 412B are respectively connected to the input waveguide 411 and the output waveguide 413. The Mach-Zehnder interferometer is configured by the input waveguide 411, the branching waveguides 412A and 412B, and the output waveguide 413. The modulation electrode 414 is formed between the branching waveguides 412A and 412B. The bias electrode 415 is formed on the branching waveguide 412B. For example, the Mach-Zehnder type optical modulator 41 is possible to employ an LN modulator having the respective waveguides and the respective electrodes formed on an X-cut LN substrate. By the above-described configuration, the Mach-Zehnder type optical modulator 41 becomes possible to operate in push-pull driving so that the generation of chirp can be zero. Meanwhile, it is also possible to use other electrode configurations capable of the push-pull driving. In addition, a Z-cut substrate may be used as the LN substrate. In a case in which the Z-cut LN substrate is used, the chirp amount increases more than a case in which the X-cut LN substrate is used, but the chirp amount can be suppressed by employing a configuration of the modulation electrodes in which a signal electrode 416 is provided on one of the two branching waveguides (branching waveguide 412A), and an earth electrode 417 is provided on the other branching waveguide (branching waveguide 412B), using a Z-cut LN substrate 410, as illustrated in FIGS. 5A and 5B.

Here, the LN modulator that is used as the Mach-Zehnder optical type modulator 41 is simply an example of the optical modulator, and other optical modulators such as a modulator in which a semiconductor such as InP is used may be used as the Mach-Zehnder type optical modulator 41.

The phase adjuster 43 adjusts the phase of the modulation signal SIG2 to match the phases between an optical pulse train (described later) from the dispersion compensator 30 and the phase (timing) of the modulation signal SIG2 from the signal generator 60. An output of the phase adjuster 43 is connected to the modulation electrode 414 in the Mach-Zehnder type optical modulator 41.

The bias voltage supplier 45 supplies a predetermined bias voltage to the Mach-Zehnder type optical modulator 41. An output of the bias voltage supplier 45 is connected to the bias electrode 415 in the Mach-Zehnder type optical modulator 41.

The first optical amplifier 51 amplifies an optical pulse (described later) output from the optical intensity modulator 40 toward the power which makes a non-linear phenomenon in the non-linear compressor 52 occur. As the first optical amplifier 51, for example, an erbium-doped fiber amplifier (EDFA) can be used.

The non-linear compressor 52 is an apparatus compressing an optical pulse, and a fiber module configured to be alternately connected to highly non-linear fibers and highly dispersed fibers is used as an example. The lengths of the respective fibers are set so as to satisfy the adiabatic compression conditions. Then, the non-linear compressor 52 adiabatically compresses (soliton-compression) an optical pulse by increasing the peak power with compressing the pulse width of the optical input pulse.

A second optical amplifier 53 amplifies an optical pulse compressed using the non-linear compressor 52 toward a power required as a final output power of the optical pulse-generator 1. An optical pulse input to the second optical amplifier 53 is compressed to an extremely narrow pulse width by the non-linear compressor 52, and therefore the spectrum bandwidth is enlarged up to approximately 40 nm. Then, an optical amplifier capable of amplification in a broad bandwidth may be used as the second optical amplifier 53.

Next, the operation of the optical pulse-generator 1 configured as described above will be described.

A light generated from the light source 10 is input to the Mach-Zehnder type optical modulator 21 in the optical frequency comb generator 20. In the Mach-Zehnder type optical modulator 21, the light is branched from the input waveguide 211 to the branching waveguides 212A and 212B, and propagates through the respective branching waveguides. At this time, while the light propagates through the branching waveguides 212A and 212B, the phase of propagating light changes in accordance with electric fields from the modulation electrodes 214A and 214B, and the bias electrode 215. In addition, the light subjected to the phase changes are multiplexed again in the output waveguide 213.

Here, when the amplitude and frequency of the input light to the Mach-Zehnder type optical modulator 21 are represented by $E_0$ and $\omega_0$ respectively and the phase changes of the propagating light in the branching waveguides 212A and 212B are represented by $\theta_1$ and $\theta_2$ respectively, the change over time of the amplitude of the light combined in the output waveguide 213, that is, the output light from the optical frequency comb generator 20 (the output light from the Mach-Zehnder type optical modulator 21), E(t), is expressed by the following formula (1).

$$E(t)=E_0[\sin(\omega_0 t+\theta_1)+\sin(\omega_0 t+\theta_2)]/2 \qquad (1)$$

Here, $$\theta_1=A_1 \sin(\omega_m t)+B_1 \qquad (2)$$

$$\theta_2=A_2 \sin(\omega_m t)+B_2 \qquad (3)$$

$$\omega_m=2\pi f_m \qquad (4)$$

$A_1$: the amplitude of modulation supplied to the propagating light through the branching waveguide 212A by the modulation electrode 214A $A_2$: the amplitude of modulation supplied to the propagating light through the branching waveguide 21213 by the modulation electrode 214B $B_1$: the phase supplied to the propagating light through the branching waveguide 212A by the bias electrode 215

$B_2$: the phase supplied to the propagating light through the branching waveguide 212B by the bias electrode 215

$f_m$: the modulation frequency of the modulation signal SIG1 generated by the signal generator 60.

Based on the above-described formula (1), the power P(t) and frequency D(t) of the output light from the optical frequency comb generator 20 can be expressed by the following formulae (5) and (6) respectively.

$$P(t)=P_0[1+\cos\{\Delta A \sin(\omega_m t)+\Delta\theta\}]/2 \qquad (5)$$

$$\omega(t)=\omega_0+\omega_m A \sin(\omega_m t) \qquad (6)$$

Here, $$\Delta A = A_1 - A_2 \quad (7)$$

$$\Delta\theta = B_1 - B_2 \quad (8)$$

$$A = (A_1 + A_2)/2 \quad (9).$$

In addition, $P_0$ represents the power of the input light to the Mach-Zehnder type optical modulator 21.

Figure 2:
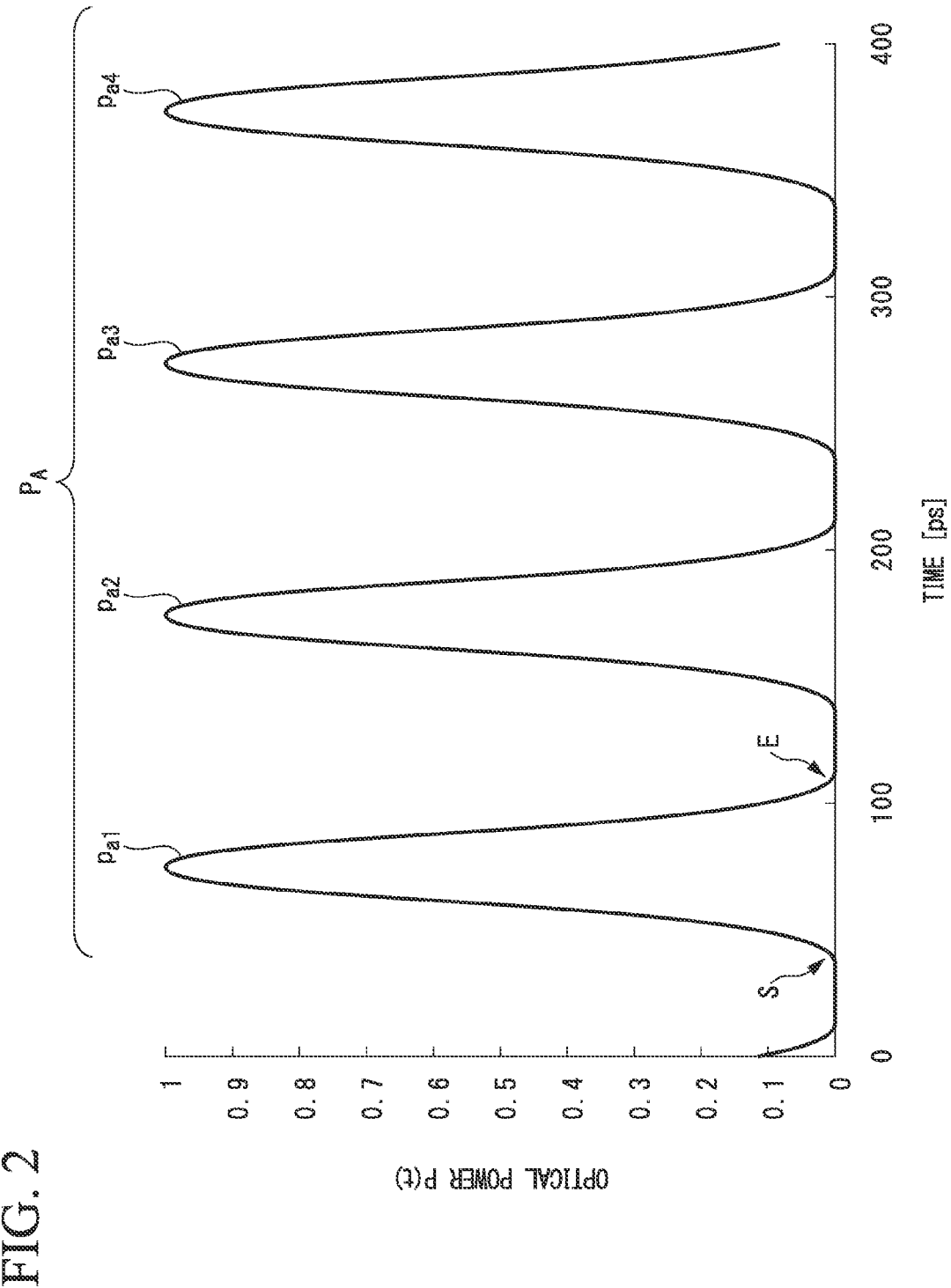
FIG. 2 is a view schematically illustrating the power P(t) of output light from an optical frequency comb generator.

In FIG. 2, the power P(t) of the output light from the optical frequency comb generator 20 is schematically illustrated. Here, FIG. 2 illustrates an example of $f_m$=10 GHz. From FIG. 2, it is found that light output from the optical frequency comb generator 20 turns into an optical pulse train $P_A$ in which a plurality of optical pulses $p_{a1}$, $P_{a2}$, $P_{a3}$, $P_{a4}$, . . . are aligned with the same intervals of time. In the example of FIG. 2, the time intervals between the respective optical pulses are 100 ps (repetition frequency 10 GHz), and the pulse width is approximately 50 ps. Meanwhile, according to the above-described formula (6), the frequency increases from the front edge S to the rear edge E of the optical pulse (in accordance with increasing the time t) in each of the optical pulses. That is, each of the optical pulses output from the optical frequency comb generator 20 has a positive chirp.

Here, the above-described formula (5) shows that the waveform P(t) of the optical pulse changes depending on the values of $\Delta A$ and $\Delta\theta$. This means, depending on the values of $\Delta A$ and $\Delta\theta$, that the waveform of the optical pulse may be strained. It is known that it is accepted satisfying the following formulae (10) and (11) as one of the conditions for obtaining an optical pulse with no strain described above (for example, refer to Japanese Laid-open Patent Publication No. 2007-248660 and Japanese Laid-open Patent Publication No. 2010-169326).

$$\Delta A = 0.5\pi \quad (10)$$

$$\Delta\theta = 0.5\pi \quad (11)$$

Therefore, when the amplification factors of the amplifier 23 and the variable amplifier 24 are set so that the modulation amplitude by the modulation signal SIG1 applied to the modulation electrodes 214A and 214B satisfies the condition of the formula (10), and furthermore, the bias voltage is set so that the phase supplied by the bias voltage applied to the bias electrode 215 satisfies the condition of the formula (11), it is possible to turn the output light from the optical frequency comb generator 20 into an optical pulse train in which optical pulses with no strain are aligned (FIG. 2).

Figure 3:
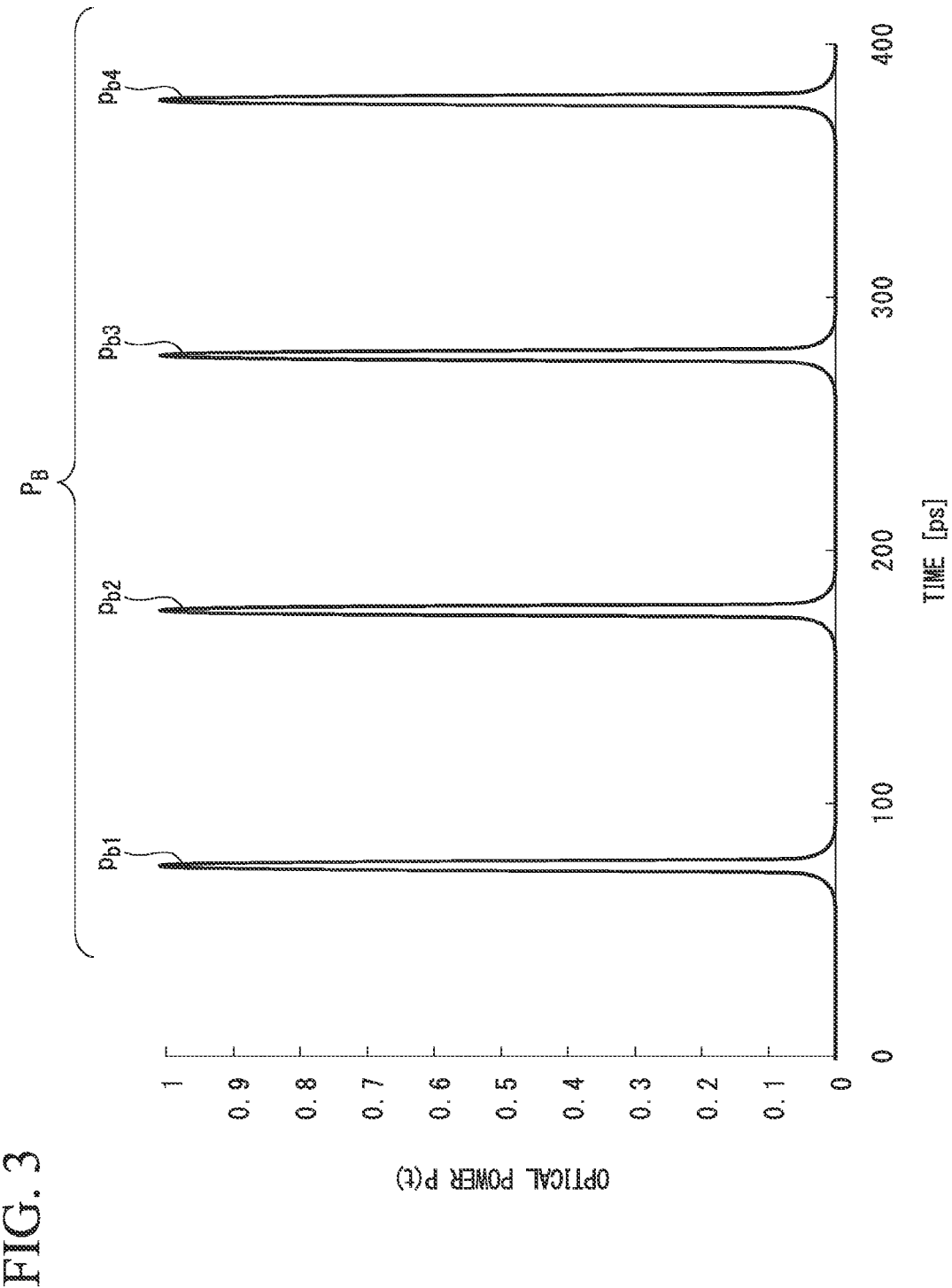
FIG. 3 is a view schematically illustrating the power P(t) of output light from a dispersion compensator.

In the above-described manner, an optical pulse output from the optical frequency comb generator 20 is input to the dispersion compensator 30, and is compressed. As described above, the optical pulse from the optical frequency comb generator 20 has a positive chirp. In order to compress the optical pulse, the dispersion compensator 30 employs an optical fiber having dispersion characteristics which have large group velocity against optical components of a longer wavelength (lower frequency) range (the front-half part of the optical pulse) and small group velocity against optical components of a shorter wavelength (higher frequency) range (the rear-half part of the optical pulse). For example, it is possible to use a single-mode fiber for telecommunication at 1.3 μm wavelength band which has linear dispersion characteristics in which the dispersion becomes zero at 1.3 μm wavelength band. The width of each optical pulse becomes narrower by passing through the dispersion compensator 30 which has above-described characteristics. In FIG. 3, the power P(t) of the output light from the dispersion compensator 30 is schematically illustrated. As illustrated in FIG. 3, the light output from the dispersion compensator 30 turns into an optical pulse train $P_B$ in which compressed optical pulses $p_{b1}$, $p_{b2}$, $p_{b3}$, $p_{b4}$, . . . are aligned. For example, the pulse width in each optical pulse that has passed through the dispersion compensator 30 is approximately 2.5 ps.

The light (optical pulse train $P_B$) output from the dispersion compensator 30 in the above-described manner is input to the optical intensity modulator 40, and is intensity-modulated by the modulation signal SIG2 in the Mach-Zehnder type optical modulator 41. The signal pattern of the modulation signal SIG2 that drives the Mach-Zehnder type optical modulator 41 is set to a signal pattern that outputs only specific part of optical pulses configuring the optical pulse train $P_B$ from the Mach-Zenhder type optical modulator 41. That is, when driven by the modulation signal SIG2, the Mach-Zehnder type optical modulator 41 operates so as to pass the above-described specific optical pulses and cut other optical pulses. The above-described signal pattern can be set to an arbitrary pattern in accordance with a desired optical pulse train output from the optical pulse-generator 1.

Figure 4:
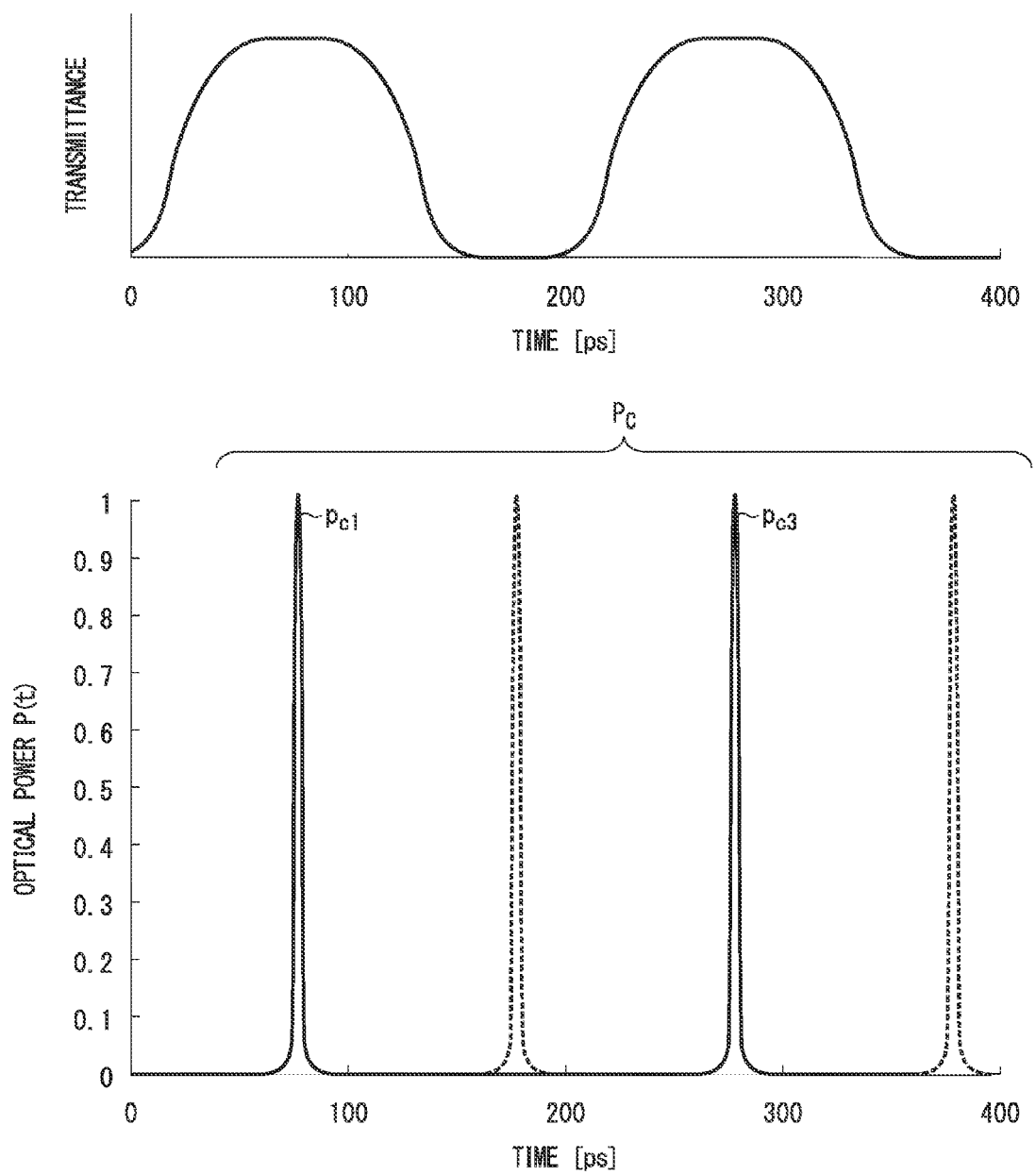
FIG. 4 are views schematically illustrating a change of the transmittance of a Mach-Zehnder type optical modulator over time and the power P(t) of output light from a optical intensity modulator.

As an example, FIG. 4 schematically illustrates the change over time of the transmittance of the Mach-Zehnder type optical modulator 41 and the power P(t) of the output light from the optical intensity modulator 40 in a case of using the half-divided modulation signal SIG1 as the modulation signal SIG2. Since the frequency of the modulation signal SIG2 is a half of the frequency of the modulation signal SIG1, the transmittance of the Mach-Zehnder type optical modulator 41 in this example alternates between a high transmittance and a low transmittance with a repetition period which is two times of the repetition period of the optical pulse input to the optical intensity modulator 40 as illustrated in FIG. 4. Therefore, when the Mach-Zehnder type optical modulator 41 is driven by the above-described modulation signal SIG2, a series of optical pulses configuring the optical pulse train $P_B$ are passed through the Mach-Zehnder type optical modulator 41 or are cut by the Mach-Zehnder type optical modulator 41 alternatively. That is, as illustrated in FIG. 4, an optical pulse train $P_c$ made up of optical pulses $p_{c1}$, $p_{c3}$, $p_{c5}$, . . . that are obtained by carving in every other optical pulse configuring the optical pulse train $P_B$ is output from the Mach-Zehnder type optical modulator 41. The time intervals between the respective optical pulses are 200 ps (repetition frequency 5 GHz) as illustrated in FIG. 4. Meanwhile, in FIG. 4, the optical pulses expressed using dotted lines indicate optical pulses carved (cut) by the Mach-Zehnder type optical modulator 41.

As described above, in the example of FIG. 4, it is possible to convert (decrease in this case) the repetition frequency of the optical pulses into one half by carving optical pulses.

In addition, similarly, when a signal which the modulation signal SIG1 divides into, for example, a fourth or an eighth is used as the modulation signal SIG2, it is possible to convert (decrease in this case) the repetition frequency of the optical pulses into a fourth or an eighth respectively.

Therefore, it is possible to change variously the repetition frequency of the optical pulse output from the optical intensity modulator 40 by appropriately selecting the frequency of the modulation signal SIG2 (the frequency obtained by dividing the frequency of the modulation signal SIG1 by an integer).

Furthermore, the signal pattern of the modulation signal SIG2 may be set to an arbitrary pattern as long as the signal pattern is in synchronization with the modulation signal SIG1. Then, it is possible to output arbitrary optical pulses from the optical intensity modulator 40 in accordance with the signal pattern in the optical pulses $p_{b1}$, $p_{b2}$, $P_{b3}$, $p_{b4}$, . . . configuring the optical pulse train $P_B$ input to the optical intensity modulator 40. That is, it is possible to generate an optical pulse train with an arbitrary pattern by appropriately setting the signal pattern of the modulation signal SIG2.

The optical pulse output from the optical intensity modulator 40 in the above-described manner is input to the optical pulse compressor 50, and is compressed. Then, it is possible to further narrow the pulse width of the optical pulse up to approximately 0.2 ps, and to generate a so-called femtosecond pulse.

As described above, according to the optical pulse-generator 1 of the first embodiment, it is possible to generate an optical pulse train with an arbitrary pattern, and furthermore, to change the repetition frequency of the optical pulse by carving optical pulses in accordance with the modulation signal SIG2 in the optical intensity modulator 40.

In addition, since the Mach-Zehnder type optical modulators 21 and 41 are configured by the LN modulators, the optical pulse-generator 1 of the first embodiment is capable of operating throughout a broad bandwidth in a range of several MHz to several tens of GHz (for example, in a range of approximately 10 MHz up to approximately 40 GHz). In addition, according to the above-described formulae (5) and (6), since the optical pulse output from the optical frequency comb generator 20 does not contain non-linear chirp effectively, it is possible to highly accurately compensate dispersion by the dispersion compensator 30 having linear dispersion, and thus the optical pulse-generator 1 is capable of generating a high-quality optical pulse with less deterioration.

As described above, an embodiment (the first embodiment) of the present invention has been described in detail with reference to the accompanying drawings, but the specific configuration is not limited thereto, and it is possible to modify the various designs without departing from the scope and the like within the present invention.

Figure 6A:
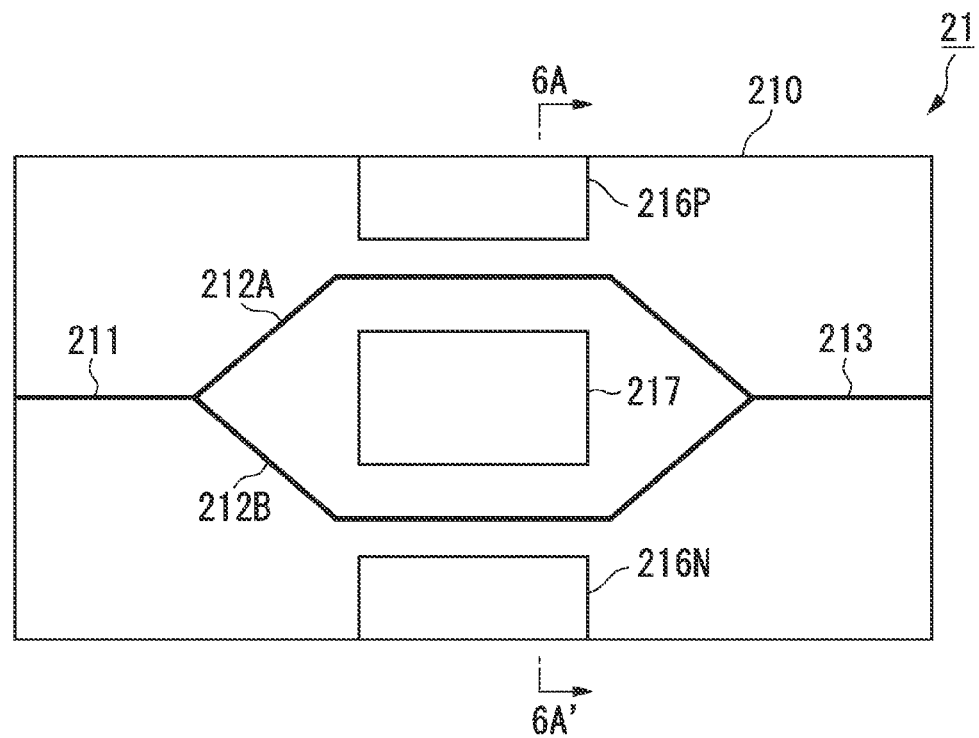
FIG. 6A is a view illustrating an electrode layout in a Mach-Zehnder type optical modulator 21 in which an X-cut LN substrate is used.
Figure 6B:
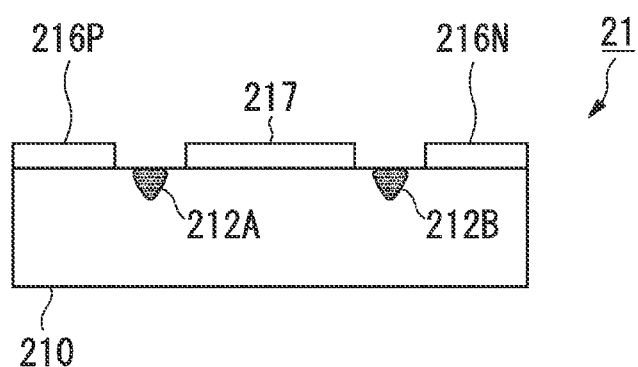
FIG. 6B is a cross-sectional view cut along the line 6A-6A' in FIG. 6A.

For example, the Mach-Zehnder type optical modulator 21 may be configured using an X-cut LN substrate. In this case, employing the configuration of the modulation electrodes in which a ground electrode 217 is provided between the two branching waveguides 212A and 212B using an X-cut LN substrate 210, and furthermore, a signal electrode 216P applying a positive voltage and a signal electrode 216N applying a negative voltage are provided with the two branching waveguides 212A and 212B interposed there between as illustrated in FIGS. 6A and 6B, it is possible to generate an optical pulse train (FIG. 2) in which the conditions of the formulae (10) and (11) are satisfied and optical pulses without strain are aligned as the same manner as described above.

Figure 9:
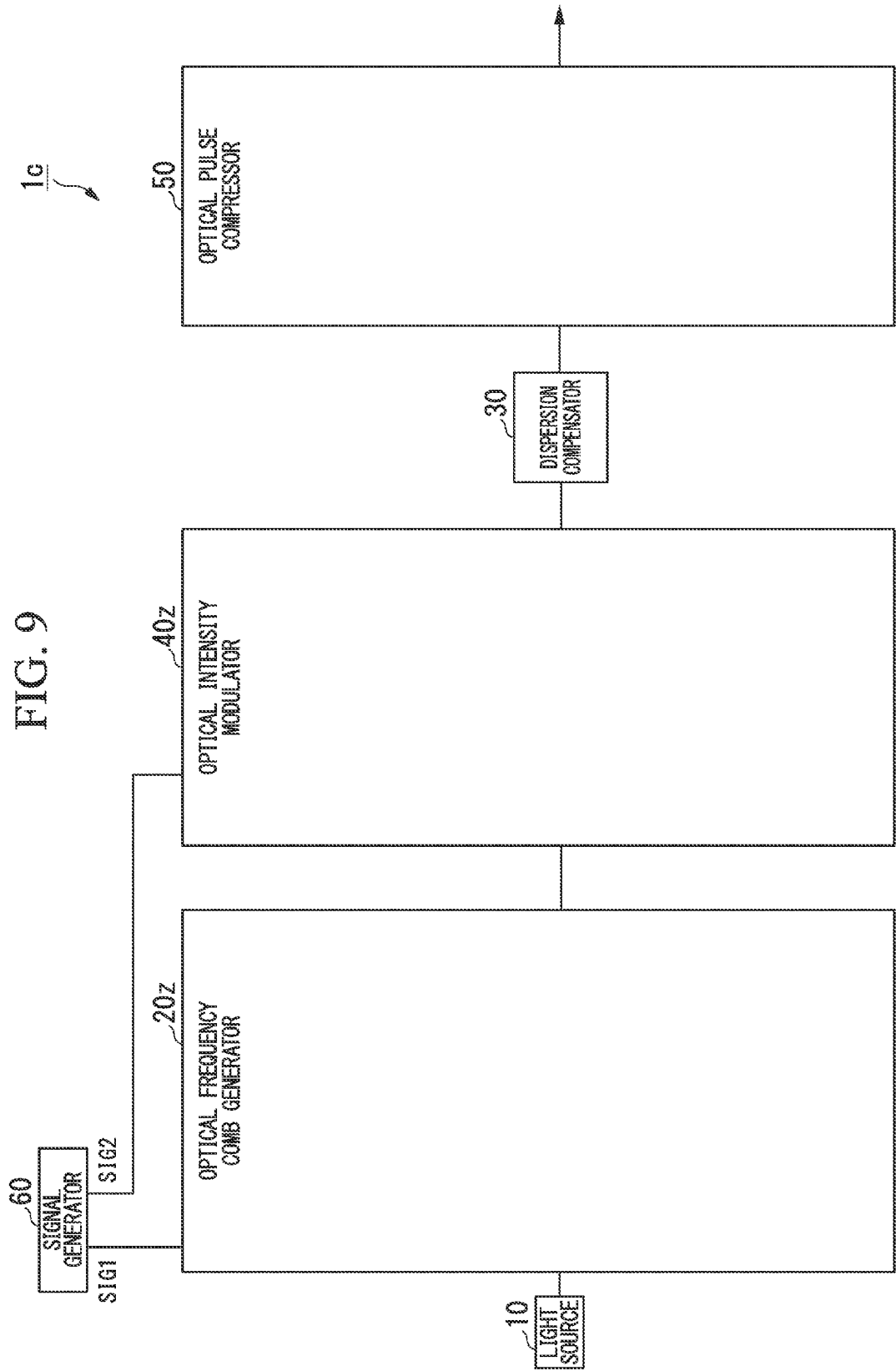
FIG. 9 is a view illustrating a configuration of an optical pulse-generator according to an embodiment (fourth embodiment) of the present invention.

In addition, the dispositions of the dispersion compensator 30 and the optical intensity modulator 40 may be exchanged (refer to FIG. 9 illustrated below). However, a high-quality optical pulse with less waveform deterioration can be obtained by a disposition in which the dispersion compensator 30 is disposed ahead of the optical intensity modulator as illustrated in FIG. 1. The reason is as described below. When the optical intensity modulator 40 is disposed ahead of the dispersion compensator, an optical pulse (FIG. 2) having a broader width before the dispersion is compensated is input to the optical intensity modulator 40 and the optical pulse is done intensity modulation by passing through the optical intensity modulator 40 having a transmittance changing over time as illustrated in FIG. 4. However, since a part of the tail of the optical pulse with a broad width attenuates and disappears in a time slot in which the transmittance decreases as described in FIG. 4, desired dispersion compensation becomes impossible when the optical pulse passes through the dispersion compensator 30 behind the optical intensity modulator, and consequently, the waveform of the optical pulse is strained. On the other hand, in a case in which the dispersion compensator 30 is disposed ahead of the optical intensity modulator, an optical pulse to be input to the optical intensity modulator 40 has already been compressed as illustrated in FIG. 3, and the tail part of the optical pulse with a narrower pulse width like this is not affected by the time slot in which the transmittance decreases as illustrated in FIG. 4, and therefore the waveform of the optical pulse does not deteriorate, and it becomes possible to obtain a high-quality optical pulse.

In addition, as the driving condition for the optical frequency comb generator 20, the following formula (12) may be used instead of the formulae (10) and (11) (refer to Japanese Laid-open Patent Publication No. 2007-248660).

$$\Delta A + \Delta \theta = \pi \qquad (12)$$

In addition, for example, when the driving conditions of $\Delta A=0.5\pi$ and $\Delta\theta=1.5\pi$ are used, an optical pulse having a negative chirp in which the frequency decreases from the front end S (refer to FIG. 2) toward the rear end E (refer to FIG. 2) of the optical pulse is output from the optical frequency comb generator 20. In this case, a dispersion compensator having dispersion characteristics opposite to the above-described dispersion characteristics may be employed as the dispersion compensator 30.

In addition, a push-pull driving method may be applied to the Mach-Zehnder type optical modulator 41 in the optical intensity modulator 40. In a case in which the push-pull driving method is used, amount of the phase variations of the two branching waveguides have equal absolute values but opposite signs, and therefore the chirp applied to the optical pulse by the Mach-Zehnder type optical modulator 41 becomes zero. Therefore, the modulation by the Mach-Zehnder type optical modulator 41 does not have any influence on the waveform of the optical pulse subjected to the dispersion compensation by the dispersion compensator 30, and the waveform deterioration of the optical pulse can be decreased.

<Configuration Examples (1) to (4) of the First Embodiment>

Hereinafter, Configuration Examples (1) to (4) of the first embodiment will be described.

(1) It is possible to provide an optical pulse-generator (the optical pulse-generator 1 in Configuration Example (1)) including a first LN modulator (the Mach-Zehnder type optical modulator 21 in the optical frequency comb generator 20 in Configuration Example (1)) configured to modulate input light using a first modulation signal (the modulation signal SIG1 in Configuration Example (1)) to generate optical pulses, a dispersion compensator (the dispersion compensator 30 in Configuration Example (1)) configured to compensate the chirp of the above-described optical pulse, and a second LN modulator (the Mach-Zehnder type optical modulator 41 in the optical intensity modulator 40 in Configuration Example (1)) configured to output specific part of the optical pulses by modulating the above-described optical pulses using a second modulation signal (the modulation signal SIG2 in Configuration Example (1)) synchronizing with the first modulation signal and having a signal pattern that is set to output only the specific part of the above-described optical pulses.

(2) It is possible to provide the optical pulse-generator according to the above-described (1), in which the above-described dispersion compensator is disposed ahead of the above-described second LN modulator.

(3) It is possible to provide the optical pulse-generator according to the above-described (1) or (2) including an optical pulse compressor (the optical pulse compressor 50 in Configuration Example (3)) configured to perform a soliton compression for the optical pulse output from the above-described second LN modulator.

(4) It is possible to provide an optical pulse-generating method including a step of modulating input light using a first modulation signal to generate optical pulses, a step of compensating the chirp of the above-described optical pulse, and a step of outputting specific part of optical pulses by modulating the optical pulses using a second modulation signal synchronizing with the first modulation signal and having a signal pattern that is set to output only the specific part of the above-described optical pulses.

[Second Embodiment]

Figure 7:
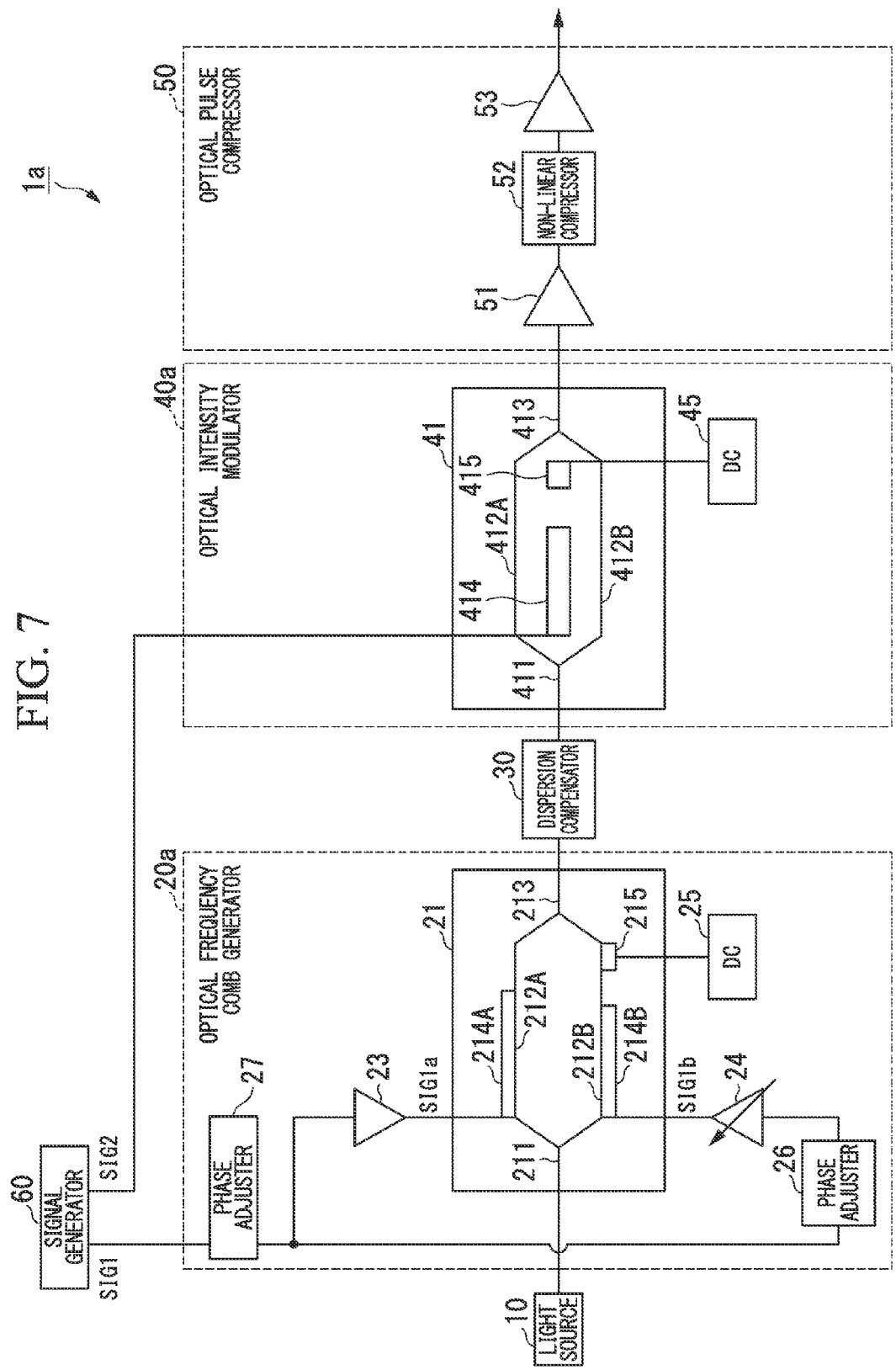
FIG. 7 is a view illustrating a configuration of an optical pulse-generator according to an embodiment (second embodiment) of the present invention.

FIG. 7 is a view illustrating a configuration of an optical pulse-generator 1a according to an embodiment (second embodiment) of the present invention. Here, comparing with the configuration of the optical pulse-generator 1 of the first embodiment illustrated in FIG. 1, the configuration of the optical pulse-generator 1a of the second embodiment is the same as that of the optical pulse-generator 1 except for the configurations of an optical frequency comb generator and an optical intensity modulator.

Hereinafter, the different aspects of the optical pulse-generator 1a of the second embodiment from the optical pulse-generator 1 of the first embodiment illustrated in FIG. 1 will be described in detail, but the same aspects will not be described in detail by affixing the same reference signs as those for the above-described embodiment (first embodiment).

Comparing with the optical frequency comb generator 20 in the first embodiment illustrated in FIG. 1, an optical frequency comb generator 20a included in the optical pulse-generator 1a of the second embodiment further includes a phase adjuster 27 on the signal generator 60 side from the amplifier 23 and the phase adjuster 26. An output of the signal generator 60 that outputs the modulation signal SIG1 is connected to the phase adjuster 27 in the optical frequency comb generator 20a. The modulation signal SIG1 output from the signal generator 60 is input to the amplifier 23 through the phase adjuster 27, and furthermore, is input to the variable amplifier 24 through the phase adjuster 27 and the phase adjuster 26.

In addition, compared with the optical intensity modulator 40 in the first embodiment illustrated in FIG. 1, an optical intensity modulator 40a included in the optical pulse-generator 1a of the second embodiment does not include a phase adjuster (a device corresponding to the phase adjuster 43 illustrated in FIG. 1). An output that outputs the modulation signal SIG2 of the signal generator 60 is connected to the modulation electrode 414 in the optical intensity modulator 40a. The modulation signal SIG2 output from the signal generator 60 is input to the modulation electrode 414.

Here, the phase adjuster 27 included in the optical frequency comb generator 20a adjusts the phase of the modulation signal SIG1 so that the phase (timing) of an optical pulse train from the dispersion compensator 30 is matched with that of the modulation signal SIG2 from the signal generator 60. An output of the phase adjuster 27 is connected to the amplifier 23 and the phase adjuster 26.

As described above, in the optical pulse-generator 1 of the first embodiment illustrated in FIG. 1, the difference between the phase relating to the modulation signal SIG1 and the phase relating to the modulation signal SIG2 is adjusted by the phase adjuster 43 in the optical intensity modulator 40; however, in the optical pulse-generator 1a of the second embodiment, the difference between the phase relating to the modulation signal SIG1 and the phase relating to the modulation signal SIG2 is adjusted by using the phase adjuster 27 in the optical frequency comb generator 20a (for example, adjustment of synchronization).

As described above, in the optical pulse-generator 1a of the second embodiment, the phase adjuster 27 for adjusting the difference between the phase relating to a clock signal (modulation signal SIG1) and the phase relating to a gate signal (modulation signal SIG2) is disposed not in a gate signal path in the optical intensity modulator 40a functioning as a pulse picker that performs pulse picking (the carving of pulses) but in a clock signal path in the optical frequency comb generator 20a generating a standard optical pulse train (optical frequency comb).

In the optical pulse-generator 1a of the second embodiment, the phase adjuster 27 for adjusting the timings between the clock signal and the gate signal is installed in the clock signal path (and outside the gate signal path). By using the phase adjuster 27, the relative timing between the clock signal and the gate signal are adjusted by changing the length of transmission path of the clock signal and the pulse picking is performed.

Meanwhile, for example, the phase adjuster 27 may have approximately 1 dB to approximately 3 dB loss for an RF signal, but the loss can be compensated by increasing the gain of the amplifier 23 or the variable amplifier 24.

As a specific example, when the clock frequency (the frequency of the clock signal) in the optical frequency comb generator 20a is 10 GHz, the bandwidth of the phase adjuster 27 may be in a range of approximately 9 GHz to approximately 11 GHz. This is because the clock signal is, for example, a sinusoidal wave, and only includes a single frequency.

When the phase of the clock signal is adjusted by the above-described phase adjuster 27, the generating time of the optical pulse from the optical frequency comb generator 20a is changed. When the generating time of the optical pulse is changed, the timing at which the optical pulse and the gate signal interact with each other in the optical intensity modulator 40a is changed. Therefore, it is possible to optimize the timing of the interaction between the optical pulse and the gate signal by optimizing the phase adjustment of the clock signal, and therefore accurate (high-quality) pulse picking can be realized.

Here, the effect of the optical pulse-generator 1a of the second embodiment will be described compared with the optical pulse-generator 1 of the first embodiment illustrated in FIG. 1. Meanwhile, here, while the effect will be described by comparing the first embodiment and the second embodiment, even the optical pulse-generator 1 of the first embodiment illustrated in FIG. 1 has a capability with sufficient effect compared with the related art.

In the optical pulse-generator 1 of the first embodiment illustrated in FIG. 1, the gate signal may be strained by the phase adjuster 43 which is placed in the gate signal path (and outside the clock signal path) of the optical intensity modulator 40. In general, the gate signal includes higher frequency components than the clock signal and is likely to be deteriorated due to an RF device. As a specific example, when the clock frequency is 10 GHz, the gate signal has frequency components of 40 GHz or more. However, in actual cases, the phase adjuster, which is usable up to 40 GHz, is almost unavailable, and even if such phase adjuster is available, it would be extremely expensive. Therefore, using an inexpensive phase adjuster can be considered, but there is a case which is not to be able to ensure a sufficient bandwidth in case of the inexpensive phase adjuster. In this case, it is considered that the gate signal is subjected to be strained so that a relatively-accurate (high-quality) pulse picking would not realize.

As described above, in the optical pulse-generator 1 of the first embodiment illustrated in FIG. 1, the gate signal in the optical intensity modulator 40 contains winder range of frequencies, for example, direct current (DC) up to approximately 40 GHz; on the other hand, in the optical pulse-generator 1a of the second embodiment, the bandwidth of the phase adjuster 27 may be, for example, in a range of approximately from 9 GHz to approximately 11 GHz.

As described above, according to the optical pulse-generator 1a of the second embodiment, it is possible to avoid the gate signal being strained by the phase adjuster, and so that accurate and high-quality pulse picking can be realized. In addition, according to the optical pulse-generator 1a of the second embodiment, the frequency bandwidth of the phase adjuster 27, may be, for example, approximately a quarter of that of the conventional technique, so that it is possible to decrease the cost of the device. In addition, according to the optical pulse-generator 1a of the second embodiment, it is possible to generate an optical pulse train with an arbitrary pattern.

As an example, in the second embodiment, the LN modulators are used respectively for the generation of the original pulse train (the Mach-Zehnder type optical modulator 21 in the optical frequency comb generator 20a) and the carving of the original pulse (the Mach-Zehnder type optical modulator 41 in the optical intensity modulator 40a) in a short-pulse light source (including an ultra short-pulse light source).

The above-described LN modulators (the Mach-Zehnder type optical modulator 21 in the optical frequency comb generator 20a and the Mach-Zehnder type optical modulator 41 in the optical intensity modulator 40a) are driven by the clock signal (modulation signal SIG1) and the gate signal (modulation signal SIG2) generated from a standard RF oscillator (for example, one unit of oscillator commonly, the signal generator 60 in the second embodiment), and the timing of both modulators can be adjusted into an appropriate state by adjusting the path length (the path length obtained by combining the path length of the modulation signal, that is the RF signal, and the optical path) from the standard RF oscillator. In the second embodiment, by adopting the configuration in which the phase of the clock signal (modulation signal SEG1) is adjusted and the phase of the gate signal (modulation signal SEG2) is not adjusted during the adjustment of the timing like the above, high-frequency devices to be used is prevented from inducing signal deterioration so that high-quality pulse picking becomes possible.

As described above, in the optical pulse-generator 1a of the second embodiment, the phase adjuster 27 for synchronizing the timings between the first LN modulator (the Mach-Zehnder type optical modulator 21 in the optical frequency comb generator 20a in the second embodiment) and the second LN modulator (the Mach-Zehnder type optical modulator 41 in the optical intensity modulator 40a in the second embodiment) is disposed in the path of the first modulation signal (the modulation signal SIG1 in the second embodiment) to be applied to the first LN modulator, and the path length of the above-described first modulation signal is adjusted.

Thus far, an embodiment (the second embodiment) of the present invention has been described in detail with reference to the accompanying drawings, but the specific configuration is not limited thereto, and it is possible to modify the various designs without departing from the scope and the like within the present invention.

[Third Embodiment]

Figure 8:
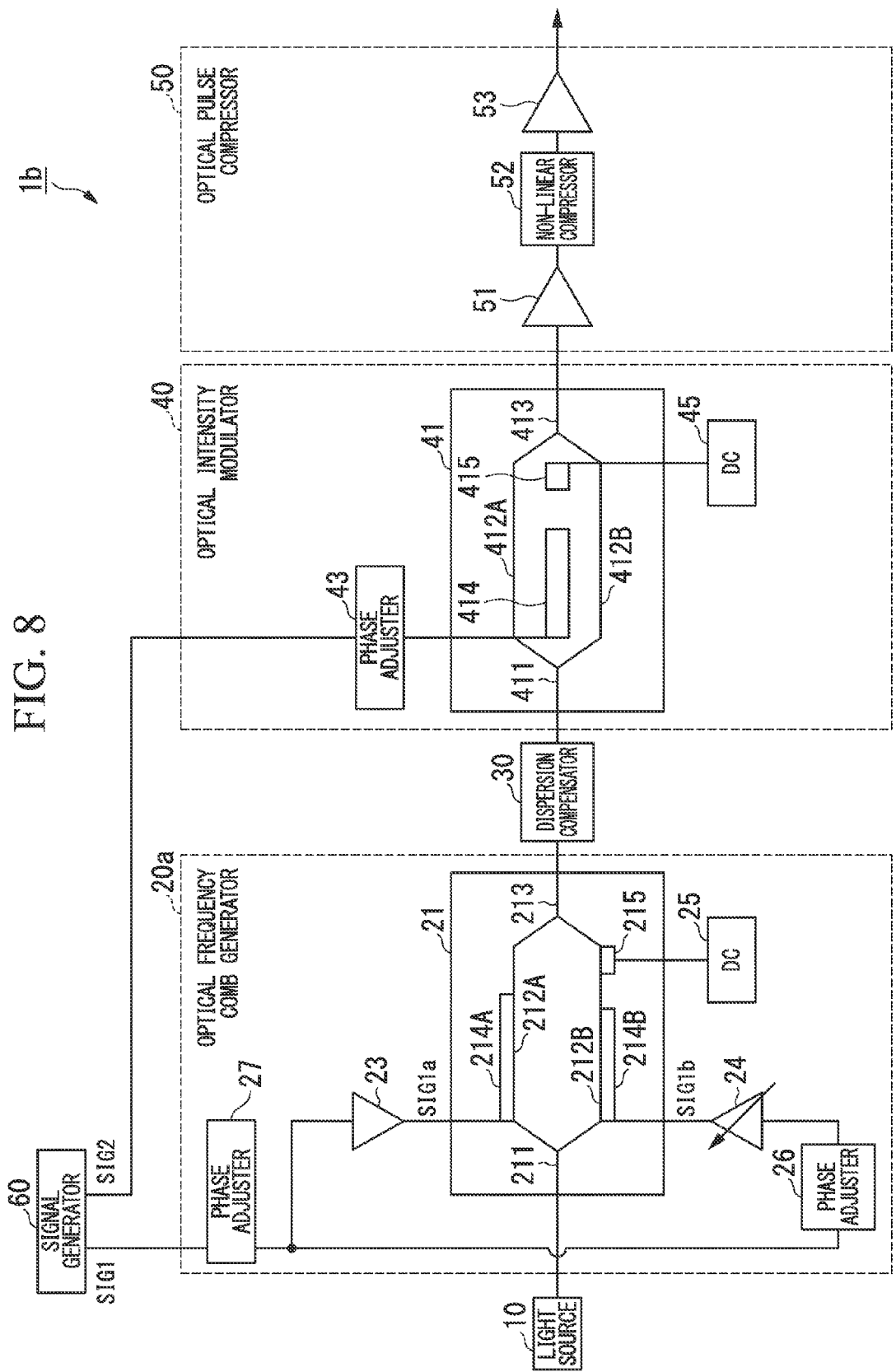
FIG. 8 is a view illustrating a configuration of an optical pulse-generator according to an embodiment (third embodiment) of the present invention.

FIG. 8 is a view illustrating a configuration of an optical pulse-generator 1b according to an embodiment (third embodiment) of the invention.

Here, comparing with the configuration of the optical pulse-generator 1 of the first embodiment illustrated in FIG. 1, the configuration of the optical pulse-generator 1b of the third embodiment is the same as that of the optical pulse-generator 1 except for the configuration of an optical frequency comb generator.

Hereinafter, the different aspects of the optical pulse-generator 1b of the third embodiment from the optical pulse-generator 1 of the first embodiment illustrated in FIG. 1 will be described in detail, but the same aspects will not be described in detail by affixing the same reference signs as those for the above-described embodiment (first and second embodiments).

Comparing with the optical frequency comb generator 20 in the first embodiment illustrated in FIG. 1, an optical frequency comb generator 20b included in the optical pulse-generator 1b of the third embodiment further includes the phase adjuster 27 located on the signal generator 60 side from the amplifier 23 and the phase adjuster 26. In addition, the output of the signal generator 60 that outputs the modulation signal SIG1 is connected to the phase adjuster 27 in the optical frequency comb generator 20a. The modulation signal SIG1 output from the signal generator 60 is input to the amplifier 23 through the phase adjuster 27, and furthermore, is input to the variable amplifier 24 through the phase adjuster 27 and the phase adjuster 26.

Here, using either or both of the phase adjuster 27 included in optical frequency comb generator 20a and the phase adjuster 43 included in the optical intensity modulator 40, either or both of phases of the modulation signal SIG1 and the modulation signal SIG2 are adjusted so that the phase (timing) of the modulation signal SIG2 is matched with that of the optical pulse train from the dispersion compensator 30. The output of the phase adjuster 27 is connected to the amplifier 23 and the phase adjuster 26.

As described above, in the optical pulse-generator 1 of the first embodiment illustrated in FIG. 1, the difference between the phase relating to the modulation signal SIG1 and the phase relating to the modulation signal SIG2 is adjusted by the phase adjuster 43 in the optical intensity modulator 40; on the other hand, in the optical pulse-generator 1b of the third embodiment, the difference between the phase relating to the modulation signal SIG1 and the phase relating to the modulation signal SIG2 is adjusted (for example, alignment with synchronizing) by either or both of the phase adjuster 27 included in the optical frequency comb generator 20a and the phase adjuster 43 included in the optical intensity modulator 40.

As described above, in the optical pulse-generator 1b of the third embodiment, the phase adjuster 27 and the phase adjuster 43 for adjusting the difference between the phase relating to the clock signal (modulation signal SIG1) and the phase relating to the gate signal (modulation signal SIG2) are disposed in the clock signal path for the optical frequency comb generator 20a generating the standard optical pulse train (optical frequency comb) and the gate signal path for the optical intensity modulator 40 functioning as a pulse picker that performs pulse picking (the carving of pulses), respectively.

As described above, according to the optical pulse-generator 1b of the third embodiment, it is possible to generate an optical pulse train with an arbitrary pattern.

Thus far, an embodiment (the third embodiment) of the present invention has been described in detail with reference to the accompanying drawings, but the specific configuration is not limited thereto, and it is possible to modify the various designs without departing from the scope and the like within the present invention.

[Fourth Embodiment]

FIG. 9 is a view illustrating a configuration of an optical pulse-generator 1c according to an embodiment (fourth embodiment) of the present invention.

Here, comparing with the configurations of the optical pulse-generators 1, 1a, and 1b of the first, second, and third embodiments illustrated in FIGS. 1, 7, and 8, the configuration of the optical pulse-generator 1c of the fourth embodiment is the same as those of the optical pulse-generator 1, 1a, and 1b of the first except for the order of the connection of the optical intensity modulator and the dispersion compensator.

Hereinafter, the different aspects of the optical pulse-generator 1c of the fourth embodiment from the optical pulse-generators 1, 1a, and 1b of the first, second, and third embodiments illustrated in FIGS. 1, 7, and 8 will be described in detail, but the same aspects will not be described in detail by affixing the same reference signs as those for the above-described embodiment (from first to third embodiments).

The optical pulse-generator 1c of the fourth embodiment includes the light source 10, an optical frequency comb generator 20z, an optical intensity modulator 40z, the dispersion compensator 30, and the optical pulse compressor 50, and is configured to connect them with the same order as described above. In addition, the optical pulse-generator 1c of the fourth embodiment includes the signal generator 60 that supplies the modulation signal SIG1 to the optical frequency comb generator 20z and supplies the modulation signal SIG2 to the optical intensity modulator 40z.

Specifically, in the optical pulse-generator 1c of the fourth embodiment, the output waveguide 213 of the Mach-Zehnder type optical modulator 21 in the optical frequency comb generator 20z and the input waveguide 411 of the Mach-Zehnder type optical modulator 41 in the optical intensity modulator 40z are connected to each other.

In addition, the output waveguide 413 of the Mach-Zehnder type optical modulator 41 in the optical intensity modulator 40z and the input end of the dispersion compensator 30 are connected to each other. In addition, the output end of the dispersion compensator 30 and an input end of the optical pulse compressor 50 are connected each other.

In addition, at least one of the optical frequency comb generator 20z and the optical intensity modulator 40z includes a phase adjuster that adjusts the difference between the phase relating to the modulation signal SIG1 and the phase relating to the modulation signal SIG2.

Specifically, as the combination of the optical frequency comb generator 20z and the optical intensity modulator 40z, it is possible to use, for example, any one of a combination of the optical frequency comb generator 20 without a phase adjuster (meanwhile, the phase adjuster 26 is installed the adjustment between the two branching waveguides 212A and 212B that is for another purpose) and the optical intensity modulator 40 with the phase adjuster 43 as illustrated in FIG. 1, a combination of the optical frequency comb generator 20a with the phase adjuster 27 and the optical intensity modulator 40a without a phase adjuster as illustrated in FIG. 7, and a combination of the optical frequency comb generator 20a with the phase adjuster 27 and the optical intensity modulator 40 with the phase adjuster 43 as illustrated in FIG. 8.

As described above, according to the optical pulse-generator 1c of the fourth embodiment, it is possible to generate an optical pulse train with an arbitrary pattern.

Thus far, an embodiment (the fourth embodiment) of the present invention has been described in detail with reference to the accompanying drawings, but the specific configuration is not limited thereto, and it is possible to modify the various designs without departing from the scope and the like within the present invention.

[Fifth Embodiment]

Figure 10:
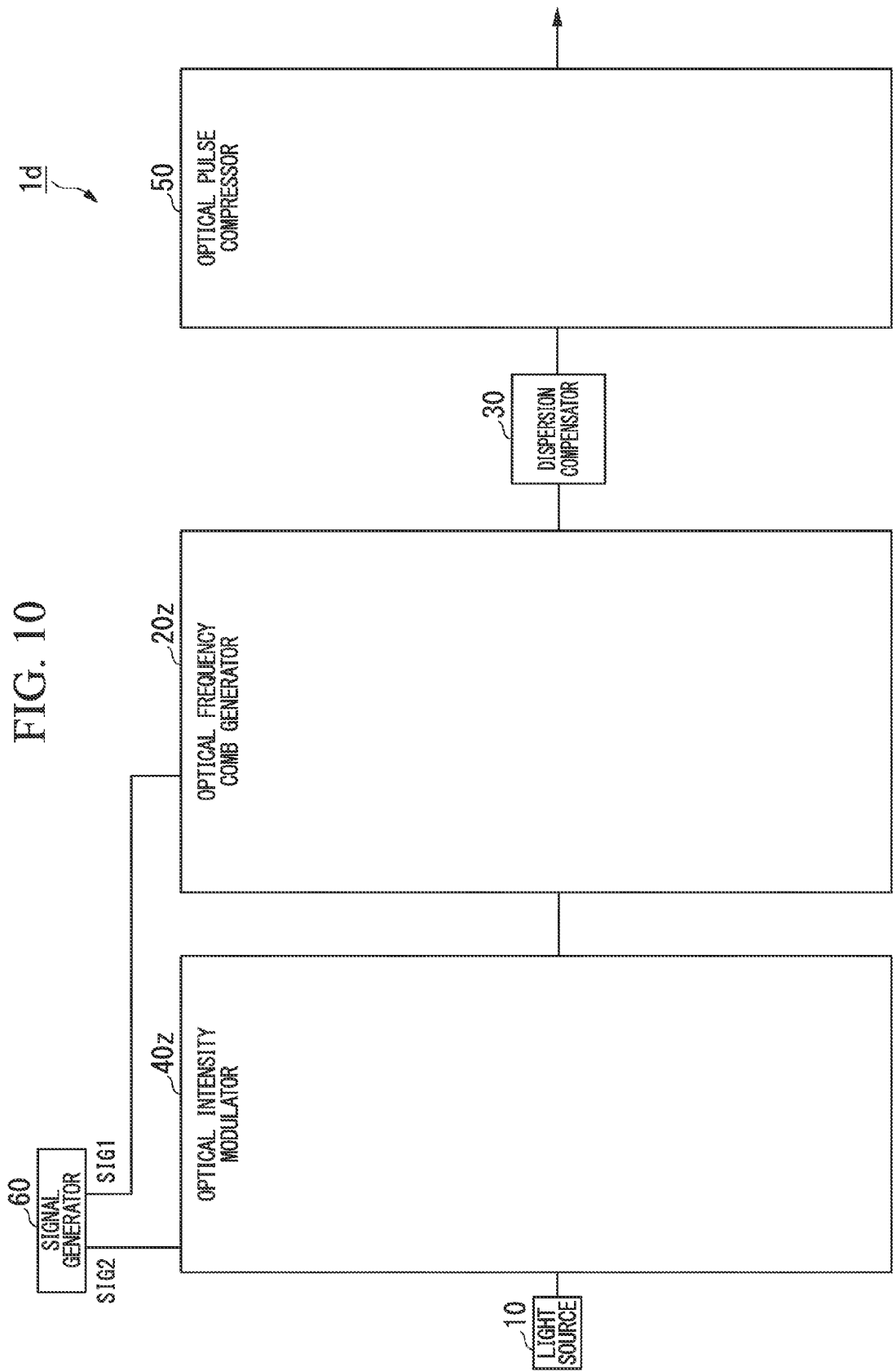
FIG. 10 is a view illustrating a configuration of an optical pulse-generator according to an embodiment (fifth embodiment) of the present invention.

FIG. 10 is a view illustrating a configuration of an optical pulse-generator 1d according to an embodiment (fifth embodiment) of the present invention.

Here, comparing with the configurations of the optical pulse-generators 1, 1a, 1b, and 1c of the first, second, third, and fourth embodiments illustrated in FIGS. 1, 7, 8, and 9, the configuration of the optical pulse-generator 1d of the fifth embodiment is the same as those of the optical pulse-generators 1, 1a, 1b, and 1c except for the order of connection among the optical frequency comb generator, the optical intensity modulator, and the dispersion compensator.

Hereinafter, the different aspects of the optical pulse-generator 1d of the fifth embodiment from the optical pulse-generators 1, 1a, 1b, and 1c of the first, second, third, and fourth embodiments illustrated in FIGS. 1, 7, 8, and 9 will be described in detail, but the same aspects will not be described in detail by affixing the same reference signs as those for the above-described embodiments (from first to fourth embodiments).

The optical pulse-generator 1d of the fifth embodiment includes the light source 10, the optical intensity modulator 40z, the optical frequency comb generator 20z, the dispersion compensator 30, and the optical pulse compressor 50, and is configured to connect them with the same order as described above. In addition, the optical pulse-generator 1d of the fifth embodiment includes the signal generator 60 that supplies the modulation signal SIG1 to the optical frequency comb generator 20z and supplies the modulation signal SIG2 to the optical intensity modulator 40z.

Specifically, in the optical pulse-generator 1d of the fifth embodiment, the output end of the light source 10 and the input waveguide 411 of the Mach-Zehnder type optical modulator 41 in the optical intensity modulator 40z are connected to each other through, for example, by an optical fiber. In addition, the output waveguide 413 of the Mach-Zehnder type optical modulator 41 in the optical intensity modulator 40z and the input waveguide 211 of the Mach-Zehnder type optical modulator 21 in the optical frequency comb generator 20z are connected to each other. In addition, the output waveguide 213 of the Mach-Zehnder type optical modulator 21 in the optical frequency comb generator 20z and the input end of the dispersion compensator 30 are connected to each other. In addition, the output end of the dispersion compensator 30 and the input end of the optical pulse compressor 50 are connected to each other.

In addition, at least one of the optical frequency comb generator 20z and the optical intensity modulator 40z includes a phase adjuster that adjusts the difference between the phase relating to the modulation signal SIG1 and the phase relating to the modulation signal SIG2.

Specifically, as the combination of the optical frequency comb generator 20z and the optical intensity modulator 40z, it is possible to use, for example, any one of a combination of the optical frequency comb generator 20 without the phase adjuster (meanwhile, the phase adjuster 26 is installed for the adjustment between the two branching waveguides 212A and 212B that is for another purpose) and the optical intensity modulator 40 with the phase adjuster 43 as illustrated in FIG. 1, a combination of the optical frequency comb generator 20a with the phase adjuster 27 and the optical intensity modulator 40a without a phase adjuster as illustrated in FIG. 7, and a combination of the optical frequency comb generator 20a with the phase adjuster 27 and the optical intensity modulator 40 without the phase adjuster 43 as illustrated in FIG. 8.

As described above, according to the optical pulse-generator 1d of the fifth embodiment, it is possible to generate an optical pulse train with an arbitrary pattern.

In addition, even in a configuration in which the optical frequency comb generator 20z is disposed behind the optical intensity modulator 40z as in the optical pulse-generator 1d of the fifth embodiment, similar to the configuration in which the optical intensity modulator 40z is disposed behind the optical frequency comb generator 20z, it is possible to obtain a sufficient performance in practice.

Thus far, an embodiment (the fifth embodiment) of the present invention has been described in detail with reference to the accompanying drawings, but the specific configuration is not limited thereto, and it is possible to modify the various designs without departing from scope and the like within the present invention.

[Configuration Examples of the Above-Described Embodiments (from First to Fifth Embodiments)]

The configuration examples of the above-described embodiments (from first to fifth embodiments) are below.

<Configuration Example 1>(Corresponding to the First to Fifth Embodiments)

An optical pulse-generator (the optical pulse-generator 1, 1a, 1b, 1c, and 1d in the first to fifth embodiments) includes a first optical modulator (the Mach-Zehnder type optical modulator 21 in the optical frequency comb generators 20, 20a, and 20z in the first to fifth embodiments) configured to modulate input light using a first modulation signal (the modulation signal SIG1 in the first to fifth embodiments) to generate optical pulses, a second optical modulator (the Mach-Zehnder type optical modulator 41 in the optical intensity modulators 40, 40a, and 40z in the first to fifth embodiments) configured to perform a modulation operation using a second modulation signal (the modulation signal SIG2 in the first to fifth embodiments) synchronizing with the first modulation signal and having a signal pattern that is set to output only specific part of the above-described optical pulses, and a dispersion compensator (the dispersion compensator 30 in the first to fifth embodiments) configured to compensate the chirp of the optical pulse output from the first above-described optical modulator.

Here, as the order of the first optical modulator, the second optical modulator, and the dispersion compensator, a variety of orders may be used as described in the above-described from first to fifth embodiments.

<Configuration Example 2>(Corresponding to the First to Fifth Embodiments)

In the above-described <Configuration Example 1> optical pulse-generator, either or both of the above-described first optical modulator and the above-described second optical modulator are LN modulator.

Meanwhile, in the above-described first to fifth embodiments, both of the first optical modulator and the second optical modulator are LN modulators; however, as other configuration examples, it is also possible to use a configuration in which one of the first optical modulator and the second optical modulator is an LN modulator, and the other is an optical modulator except an LN modulator.

<Configuration Example 3>(Corresponding to the First to Fifth Embodiments)

In the optical pulse-generator described in the above-described <Configuration Example 1> or <Configuration Example 2>, the dispersion compensator is disposed behind the first optical modulator and ahead of or behind the second optical modulator.

Here, in the first to third embodiments, the dispersion compensator 30 is disposed behind the first optical modulator (the Mach-Zehnder type optical modulator 21 in the optical frequency comb generators 20 and 20a in the first to third embodiments) and ahead of the second optical modulator (the Mach-Zehnder type optical modulator 41 in the optical intensity modulators 40 and 40a in the first to third embodiments).

In addition, in the fourth and fifth embodiments, the dispersion compensator 30 is disposed behind the first optical modulator (the Mach-Zehnder type optical modulator 21 in the optical frequency comb generator 20z in the fourth and fifth embodiments) and also behind the second optical modulator (the Mach-Zehnder type optical modulator 41 in the optical intensity modulator 40z in the fourth and fifth embodiments).

<Configuration Example 4>(Corresponding to the First to Fifth Embodiments)

The optical pulse-generator described in any one of the above-described <Configuration Example 1> to <Configuration Example 3> further includes an optical pulse compressor (the optical pulse compressor 50 in the first to fifth embodiments) configured to perform a soliton compression to an optical pulse output from a follower one of the second optical modulator and the dispersion compensator along an optical transmission direction.

<Configuration Example 5<(Corresponding to the First to Fifth Embodiments)

The optical pulse-generator described in any one of the above-described <Configuration Example 1> to <Configuration Example 4> includes a phase adjuster (the phase adjusters 27 and 43 in the first to fifth embodiments) for timing synchronization between the first optical modulator and the second optical modulator.

Here, the first embodiment includes the phase adjuster 43 in the optical intensity modulator 40 for performing the timing synchronization between the first optical modulator and the second optical modulator.

In addition, the second embodiment includes the phase adjuster 27 in the optical frequency comb generator 20a for the timing synchronization between the first optical modulator and the second optical modulator.

In addition, the third embodiment includes the phase adjuster 27 in the optical frequency comb generator 20a and the phase adjuster 43 in the optical intensity modulator 40 for performing timing synchronization between the first optical modulator and the second optical modulator. Meanwhile, for example, only one of the two phase adjusters 27 and 40 may be operated for the timing synchronization, or both of the two phase adjusters 27 and 40 may be operated for the timing synchronization.

In addition, the fourth and fifth embodiments include either or both of the phase adjuster 27 in the optical frequency comb generator and the phase adjuster 43 in the optical intensity modulator to perform the timing synchronization like the above.

<Configuration Example 6>(Corresponding to a Part of the Second, Fourth, and Fifth Embodiments)

In the optical pulse-generator described in the above-described <Configuration Example 5>, the phase adjuster is included in the path for the first modulation signal to be applied to the first optical modulator, and the phase adjuster is not included in the path for the second modulation signal to be applied to the second optical modulator.

Here, in the second embodiment, in order to perform the timing synchronization described above, the phase adjuster 27 is included in the path for the first modulation signal (the modulation signal SIG1 in the second embodiment) in the optical frequency comb generator 20a, and the phase adjuster is not included in the path for the second modulation signal (the modulation signal SIG2 in the second embodiment) in the optical intensity modulator 40a.

REFERENCE SIGNS LIST 1, 1a, 1b, 1c, 1d OPTICAL PULSE-GENERATOR
10 LIGHT SOURCE
20,20a, 20z OPTICAL FREQUENCY COMB GENERATOR
30 DISPERSION COMPENSATOR
40, 40a, 40z OPTICAL INTENSITY MODULATOR
50 OPTICAL PULSE COMPRESSOR
60 SIGNAL GENERATOR
21, 41 MACH-ZEHNDER TYPE OPTICAL MODULATOR
23 AMPLIFIER
24 VARIABLE AMPLIFIER
25, 45 BIAS VOLTAGE SUPPLIER
26, 27, 43 PHASE ADJUSTER
51, 53 OPTICAL AMPLIFIER
52 NON-LINEAR COMPRESSOR
211, 411 INPUT WAVEGUIDE
212A, 212B, 412A, 412B BRANCHING WAVEGUIDE
213, 413 OUTPUT WAVEGUIDE
214A, 214B, 414 MODULATION ELECTRODE
215, 415 BIAS ELECTRODE

The invention claimed is:

1. An optical pulse-generator comprising:
a first optical modulator configured to modulate input light using a first modulation signal to generate optical pulses;
a second optical modulator configured to perform a modulation operation using a second modulation signal synchronizing with the first modulation signal and having a signal pattern that is set to output only specific part of the optical pulses;
a dispersion compensator configured to compensate a chirp of the optical pulse output from the first optical modulator; and
an optical pulse compressor configured to perform a soliton compression to an optical pulse output from a follower one of the second optical modulator and the dispersion compensator in an optical transmission direction.

2. The optical pulse-generator according to claim 1, wherein at least one of the first optical modulator and the second optical modulator is a lithium niobate modulator.

3. The optical pulse-generator according to claim 2, wherein both of the first optical modulator and the second optical modulator are lithium niobate modulators.

4. The optical pulse-generator according to claim 3, wherein the dispersion compensator is disposed behind the first optical modulator and ahead of the second optical modulator.

5. The optical pulse-generator according to claim 3, wherein the dispersion compensator is disposed behind the first optical modulator and behind the second optical modulator.

6. The optical pulse-generator according to claim 2, wherein the dispersion compensator is disposed behind the first optical modulator and ahead of the second optical modulator.

7. The optical pulse-generator according to claim 2, wherein the dispersion compensator is disposed behind the first optical modulator and behind the second optical modulator.

8. The optical pulse-generator according to claim 2, further comprising:
a phase adjuster configured to perform the timing synchronization between the first optical modulator and the second optical modulator.

9. The optical pulse-generator according to claim 1, wherein the dispersion compensator is disposed behind the first optical modulator and ahead of the second optical modulator.

10. The optical pulse-generator according to claim 1, wherein the dispersion compensator is disposed behind the first optical modulator and behind the second optical modulator.

11. An optical pulse-generator comprising,
a first optical modulator configured to modulate input light using a first modulation signal to generate optical pulses;
a second optical modulator configured to perform a modulation operation using a second modulation signal synchronizing with the first modulation signal and having a signal pattern that is set to output only specific part of the optical pulses;
a dispersion compensator configured to compensate a chirp of the optical pulse output from the first optical modulator; and
a phase adjuster configured to perform the timing synchronization between the first optical modulator and the second optical modulator,
wherein the phase adjuster is included in a path of the first modulation signal to be applied to the first optical modulator, and the phase adjuster is not included in a path of the second modulation signal to be applied to the second optical modulator.

12. An optical pulse-generating method comprising:
an optical pulse generation step of modulating input light using a first modulation signal to generate optical pulses;
a modulation operation step of performing a modulation using a second modulation signal synchronizing with the first modulation signal and having a signal pattern that is set to output only specific part of the optical pulses; and
a chirp compensation step of compensating a chirp of the optical pulse output from the optical pulse generation step; and a phase adjustment step of performing phase adjustment for performing a timing synchronization between the optical pulse generation step and the modulation operation step, wherein the phase adjustment step is performed in a path of the first modulation signal, and the phase adjustment step is not performed in a path of the second modulation signal.

13. The optical pulse-generating method according to claim 12, wherein at least one of the optical pulse generation step and the modulation operation step is performed using a lithium niobate modulator.

14. The optical pulse-generating method according to claim 12, wherein both of the optical pulse generation step and the modulation operation step are performed using a lithium niobate modulator.

* * * * *